US 6,527,925 B1

(12) United States Patent
Batz, Jr. et al.

(10) Patent No.: US 6,527,925 B1
(45) Date of Patent: Mar. 4, 2003

(54) CONTACT ASSEMBLIES, METHODS FOR MAKING CONTACT ASSEMBLIES, AND PLATING MACHINES WITH CONTACT ASSEMBLIES FOR PLATING MICROELECTRONIC WORKPIECES

(75) Inventors: Robert W. Batz, Jr., Kalispell, MT (US); John M. Pedersen, Kalispell, MT (US); John L. Klocke, Kalispell, MT (US); LinLin Chen, Plano, TX (US)

(73) Assignee: Semitool, Inc., Kalispell, MT (US)

( * ) Notice: Subject to any disclaimer, the term of this patent is extended or adjusted under 35 U.S.C. 154(b) by 104 days.

(21) Appl. No.: 09/717,927

(22) Filed: Nov. 20, 2000

Related U.S. Application Data (63) Continuation-in-part of application No. PCT/US99/15847, filed on Jul. 12, 1999, which is a continuation of application No. 09/113,723, filed on Jul. 10, 1998, now Pat. No. 6,080,291.
(60) Provisional application No. 60/119,668, filed on Jul. 12, 1999, and provisional application No. 60/111,232, filed on Dec. 7, 1998.

(51) Int. Cl.[7] ........................ C25D 17/16; C25D 17/04; C25D 17/06
(52) U.S. Cl. ............................ 204/297.01; 204/224 R
(58) Field of Search ........................ 204/224 R, 297.01

(56) References Cited

U.S. PATENT DOCUMENTS

| 4,137,867 A | 2/1979 | Aigo ........................... 118/627 |
| 4,246,088 A | 1/1981 | Murphy et al. ............. 205/122 |
| 4,259,166 A | 3/1981 | Whitehurst .................. 204/279 |
| 4,304,641 A | 12/1981 | Grandia et al. .............. 205/96 |
| 4,341,629 A | 7/1982 | Uhlinger ..................... 210/128 |
| 4,422,915 A | 12/1983 | Wielonski et al. .......... 204/165 |
| 4,466,864 A | 8/1984 | Bacon et al. ................ 205/105 |
| 4,576,685 A | 3/1986 | Goffredo et al. ............ 205/126 |
| 4,685,414 A | 8/1987 | DiRico ......................... 118/46 |
| 4,913,085 A | 4/1990 | Vöhringer et al. .......... 118/312 |
| 5,135,636 A | 8/1992 | Yee et al. ..................... 205/96 |

(List continued on next page.)

FOREIGN PATENT DOCUMENTS

| WO | 99/25904 A | 5/1999 |
| WO | 99/25905 A | 5/1999 |
| WO | 00/03072 A | 1/2000 |
| WO | 00/32835 A | 6/2000 |

Primary Examiner—Nam Nguyen
Assistant Examiner—Erica Smith Hicks
(74) Attorney, Agent, or Firm—Perkins Coie LLP (57) ABSTRACT

Contact assemblies, electroplating machines with contact assemblies, and methods for making contact assemblies that are used in the fabrication of microelectronic workpieces. The contact assemblies can be wet-contact assemblies or dry-contact assemblies. A contact assembly for use in an electroplating system can comprise a support member and a contact system coupled to the support member. The support member, for example, can be a ring or another structure that has an inner wall defining an opening configured to allow the workpiece to move through the support member along an access path. In one embodiment, the support member is a conductive ring having a plurality of posts depending from the ring that are spaced apart from one another by gaps. The contact system can be coupled to the posts of the support member. The contact system can have a plurality of contact members projecting inwardly into the opening relative to the support member and transversely with respect to the access path. The contact members can comprise electrically conductive biasing elements, such as fingers, that have a contact site and a dielectric coating covering at least a portion of the biasing elements. The contact members can also have a raised feature configured to engage the seed-layer on the workpiece for conducting the current to the seed-layer.

32 Claims, 6 Drawing Sheets

U.S. PATENT DOCUMENTS

| | | | |
|---|---|---|---|
| 5,139,818 A | 8/1992 | Mance | 427/585 |
| 5,227,041 A | 7/1993 | Brogden et al. | 204/297.05 |
| 5,271,953 A | 12/1993 | Litteral | 427/8 |
| 5,310,580 A | 5/1994 | O'Sullivan et al. | 427/307 |
| 5,344,491 A | 9/1994 | Katou | 118/659 |
| 5,389,496 A | 2/1995 | Calvert et al. | 430/315 |
| 5,441,629 A | 8/1995 | Kosaki | 204/148 |
| 5,443,707 A | 8/1995 | Mori | 204/242 |
| 5,447,615 A | 9/1995 | Ishida | 204/224 R |
| 5,522,975 A | 6/1996 | Andricacos et al. | 204/288.1 |
| 5,550,315 A | 8/1996 | Stormont | 588/259 |
| 5,597,460 A | 1/1997 | Reynolds | 204/212 |
| 5,597,836 A | 1/1997 | Hackler et al. | 514/352 |
| 5,609,239 A | 3/1997 | Schlecker | 198/680 |
| 5,670,034 A | 9/1997 | Lowery | 205/143 |
| 5,744,019 A | 4/1998 | Ang | 205/96 |
| 5,747,098 A | 5/1998 | Larson | 427/58 |
| 5,776,327 A | 7/1998 | Botts et al. | 205/96 |
| 5,788,829 A | 8/1998 | Joshi et al. | 205/96 |
| 5,843,296 A | 12/1998 | Greenspan | 205/68 |
| 5,904,827 A | 5/1999 | Reynolds | 205/68 |
| 5,932,077 A | 8/1999 | Reynolds | 204/224 R |
| 5,985,126 A | 11/1999 | Bleck et al. | 204/212 |
| 6,001,235 A | 12/1999 | Arken et al. | 205/137 |
| 6,080,291 A | 6/2000 | Woodruff et al. | 204/297.1 |
| 6,139,712 A | 10/2000 | Patton et al. | 205/143 |
| 6,156,167 A | 12/2000 | Patton et al. | 204/270 |

CONTACT ASSEMBLIES, METHODS FOR MAKING CONTACT ASSEMBLIES, AND PLATING MACHINES WITH CONTACT ASSEMBLIES FOR PLATING MICROELECTRONIC WORKPIECES

CROSS REFERENCE TO RELATED APPLICATIONS

This application is a continuation-in-part of PCT Application No. PCT/US99/15847, filed Jul. 12, 1999, which application is a continuation of U.S. patent application Ser. No. 09/113,723, filed Jul. 10, 1998; issued as U.S. Pat. No. 6,080,291, and claims the benefit of U.S. Provisional Application Nos. 60/111,232, filed Dec. 7, 1998 and 60/119,668, filed Jul. 12, 1999; all of which are herein incorporated by reference in their entirety.

BACKGROUND

Processors, memory devices, field-emission-displays, read/right heads and other microelectronic devices generally have integrated circuits with microelectronic components. A large number of individual microelectronic devices are generally formed on a semiconductor wafer, a glass substrate, or another type microelectronic workpiece. In a typical fabrication process, one or more layers of metal are formed on the workpieces at various stages of fabricating the microelectronic devices to provide material for constructing interconnects between various components.

The metal layers can be applied to the workpieces using several techniques, such as chemical vapor deposition (CVD), physical vapor deposition (PVD), plasma-enhanced deposition processes, electroplating, and electroless plating. The particular technique for applying a metal to a workpiece is a function of the particular type of metal, the structure that is being formed on the workpiece, and several other processing parameters. For example, CVD and PVD techniques are often used to deposit aluminum, nickel, tungsten, solder, platinum and other metals. Electroplating and electroless plating techniques can be used deposit copper, solder, permalloy, gold, silver, platinum and other metals. Electroplating and electroless plating can be used to form blanket layers and patterned layers. In recent years, processes for plating copper have become increasingly important in fabricating microelectronic devices because copper interconnects provide several advantages compared to aluminum and tungsten for high-performance microelectronic devices.

Electroplating is typically performed by forming a thin seed-layer of metal on a front surface of a microelectronic workpiece, and then using the seed-layer as a cathode to plate a metal layer onto the workpiece. The seed-layer can be formed using PVD or CVD processes. The seed-layer is generally formed on a topographical surface having vias, trenches, and/or other features, and the seed-layer is generally approximately 1000 angstroms thick. The metal layer is then plated onto the seed-layer using an electroplating technique to a thickness of approximately 6,000 to 15,000 angstroms. As the size of interconnects and other microelectronic components decrease, it is becoming increasingly important that a plated metal layer (a) has a uniform thickness across the workpiece, (b) completely fills the vias/trenches, and (c) has an adequate grain size.

Electroplating machines for use in manufacturing microelectronic devices often have a number of single-wafer electroplating chambers. A typical chamber includes a container for holding an electroplating solution, an anode in the container to contact the electroplating solution, and a support mechanism having a contact assembly with electrical contacts that engage the seed-layer. The electrical contacts are coupled to a power supply to apply a voltage to the seed-layer. In operation, the front surface of the workpiece is immersed in the electroplating solution so that the anode and the seed-layer establish an electrical field that causes metal in a diffusion layer at the front surface of the workpiece to plate onto the seed-layer.

The structure of the contact assembly can significantly influence the uniformity of the plated metal layer because the plating rate across the surface of the microelectronic workpiece is influenced by the distribution of the current (the "current density") across the seed-layer. One factor that affects the current density is the distribution of the electrical contacts around the perimeter of the workpiece. In general, a large number of discrete electrical contacts should contact the seed-layer proximate to the perimeter of the workpiece to provide a uniform distribution of current around the perimeter of the workpiece. Another factor that affects the current density is the formation of oxides on the seed-layer. Oxides are generally resistive, and thus oxides reduce the efficacy of the electrical connection between the contacts and the seed-layer. Still other factors that can influence the current density are (a) galvanic etching between the contacts and the seed-layer, (b) plating on the contacts during a plating cycle, (c) gas bubbles on the seed-layer, and (d) other aspects of electroplating that affect the quality of the connection between the contacts and the seed-layer or the fluid dynamics at the surface of the workpiece. The design of the contact assembly should address these factors to consistently provide a uniform current density across the workpiece.

One type of contact assembly is a "dry-contact" assembly having a plurality of electrical contacts that are sealed from the electroplating solution. For example, U.S. Pat. No. 5,227,041 issued to Brogden et al. discloses a dry contact electroplating structure having a base member for immersion into an electroplating solution, a seal ring positioned adjacent to an aperture in the base member, a plurality of contacts arranged in a circle around the seal ring, and a lid that attaches to the base member. In operation, a workpiece is placed in the base member so that the front face of the workpiece engages the contacts and the seal ring. When the front face of the workpiece is immersed in the electroplating solution, the seal ring prevents the electroplating solution from contacting the contacts inside the base member. One manufacturing concern of dry-contact assemblies is that galvanic etching occurs between the contacts and the seed-layer when an electrolyte solution gets into the dry contact area. Galvanic etching removes the seed-layer at the interface of the contacts, which can cause a non-uniform current distribution around the perimeter of the workpiece. Therefore, even though dry-contact assemblies keep the contacts clean, they may produce non-uniform metal layers on the workpieces.

Another type of contact assembly is a "wet-contact" assembly having a plurality of electrical contacts that are exposed to the electroplating solution during a plating cycle. Because the contacts are exposed to the electroplating solution during a plating cycle, the metal in the electroplating solution also plates onto the contacts. The contacts, however, may plate at different rates such that some contacts can have a greater surface area of conductive material contacting the seed-layer. The in-situ plating of contacts can accordingly reduce the uniformity of the metal layer on the workpiece. Additionally, wet-contact assemblies must be periodically "de-plated" to remove the metal that plates onto the contacts during a plating cycle. Therefore, it would be desirable to develop a wet-contact assembly that eliminates or reduces the processing concerns associated with exposing the contacts to the electroplating solution.

SUMMARY

The present invention is generally directed toward contact assemblies, electroplating machines with contact assemblies, and methods for making contact assemblies that are used in the fabrication of microelectronic workpieces. The contact assemblies can be wet-contact assemblies or dry-contact assemblies. In one aspect of the invention, a contact assembly for use in an electroplating system comprises a support member and a contact system coupled to the support member. The support member, for example, can be a ring or another structure that has an inner wall defining an opening configured to allow the workpiece to move through the support member along an access path. In one embodiment, the support member is a conductive ring having a plurality of posts that depend from the ring and are spaced apart from one another by gaps.

The contact system can be coupled to the posts of the support member. The contact system can have a plurality of contact members projecting inwardly into the opening relative to the support member and transversely with respect to the access path. The contact members can comprise electrically conductive biasing elements, such as fingers, that have a contact site and a dielectric coating configured to expose the contact sites. In one embodiment, the contact system further comprises a conductive mounting section attached directly to the posts to define flow paths through the gaps. The contact members can project inwardly from the mounting section along a radius of the opening or at an angle to a radius of the opening to define cantilevered spring elements that can support the workpiece. The contact members can also have a raised feature configured to engage the seed-layer on the workpiece.

In operation, a workpiece is loaded into the contact assembly by inserting the workpiece through the opening of the support member until the front face of the workpiece engages the contact sites on the contact members. Because the contact members can be biasing elements that flex, the contact members flex downwardly and transversely relative to the access path so that the contact sites adequately engage the seed-layer on the workpiece even though the face of the workpiece may have vias, trenches and other topographical features. The face of the workpiece and the contact members can then be immersed in an electroplating solution while the contact assembly rotates. Because the contact members are exposed to the electroplating solution, the metal in the solution continuously plates the interface between the contact sites and the seed-layer. The plating of the contact/seed-layer interface mitigates the galvanic etching of seed-layer. Additionally, several embodiments of contact members have a dielectric coating with stepped edges adjacent to the contact site that inhibit the metal from plating over the dielectric layer. The stepped edges accordingly reduce the problems associated with de-plating the contacts. Also, in embodiments that have a raised feature on the contact members, the electroplating solution can flow more readily between the contact members and the workpiece to reduce plating on the contact members. Therefore, several embodiments of contact assemblies are expected to enhance the quality and throughput of electroplating microelectronic workpieces.

DETAILED DESCRIPTION OF SELECTED EMBODIMENTS

The following description discloses the details and features of several embodiments of contact assemblies, methods for making contact assemblies, and electroplating machines with contact assemblies for electroplating metal layers onto microelectronic workpieces. It will be appreciated that several of the details set forth below are provided to describe the foregoing embodiments in a manner sufficient to enable a person skilled in the art to make and use contact assemblies and electroplating systems in accordance with embodiments of the invention. Several of the details and advantages described below, however, may not be necessary to practice embodiments of the invention accordance with the following claims. For example, many of the embodiments described below are directed toward wet-contact assemblies, but these same devices can also be used in dry-contact assemblies as shown in PCT Application No. PCT/US99/15847. Additionally, the invention can also include additional embodiments that are within the scope of the claims but are not described in detail with respect to FIGS. 1–11.

The operation and features of the contact assemblies are best understood in light of the environment and equipment in which they can be used to electroplate workpieces. As such, several embodiments of electroplating tools and reaction chambers that can be used with the contact assemblies will be described with reference to FIGS. 1 and 2. The details and features of several embodiments of contact assemblies will then be described with reference to FIGS. 3–11.

Figure 1:
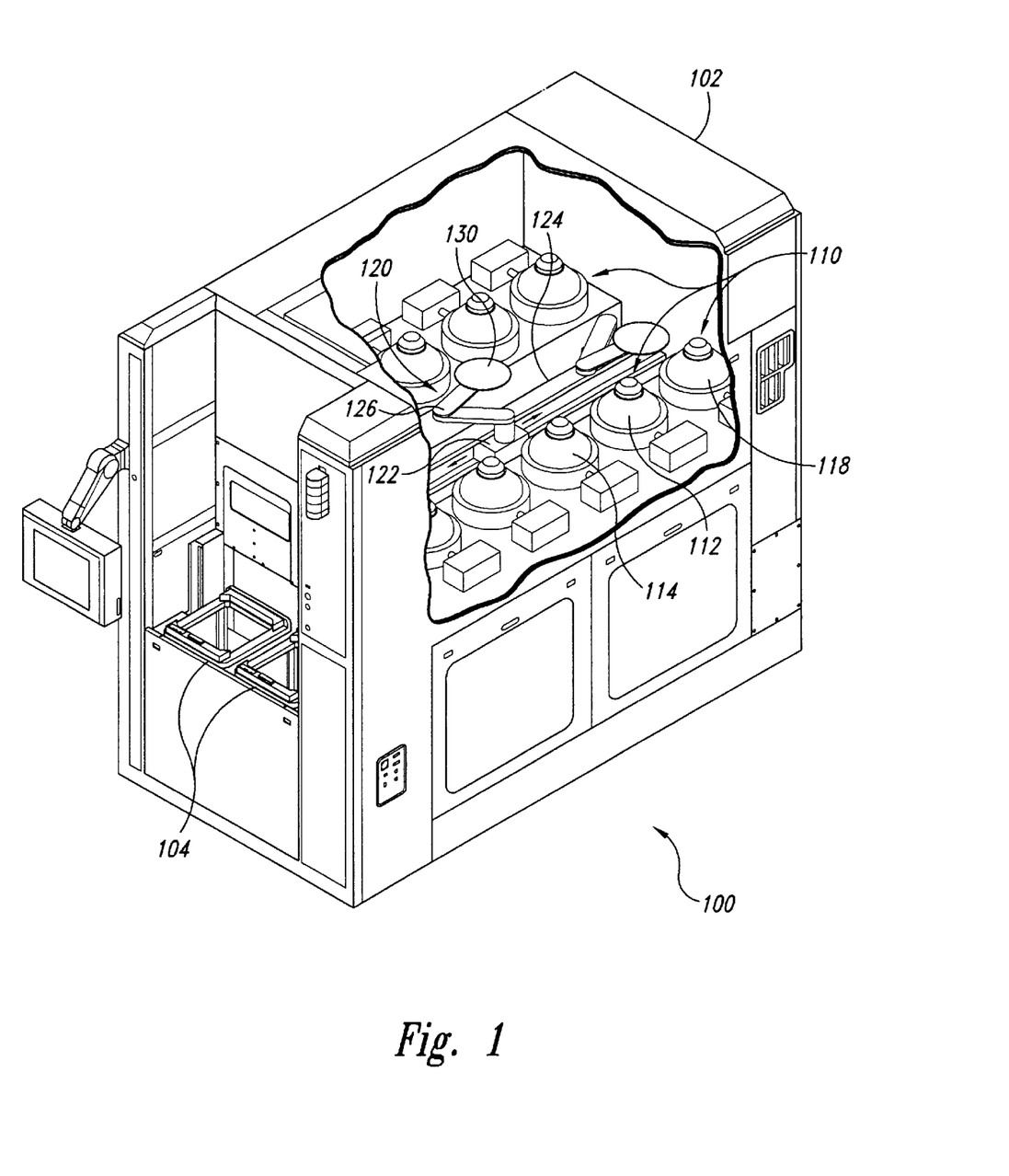
FIG. 1 is an isometric view with a cut-away portion of an electroplating machine having a contact assembly in accordance with one embodiment of the invention.

A. Selected Embodiments of Electroplating Machines and Reactor Chambers for Use With Contact Assemblies to Electroplate Metals onto Microelectronic Workpieces FIG. 1 is a front isometric view of an electroplating machine 100 in which contact assemblies in accordance with embodiments of the invention can be used. The electroplating machine 100 can include a cabinet 102, a load/unload mechanism 104 at one end of the cabinet 102, and a plurality of chambers 110 in the cabinet 102. The chambers 110 can include electroplating chambers 112, electroless plating chambers 114, and/or rapid thermal annealing chambers 118. The electroplating chambers 112 can include a contact assembly (not shown in FIG. 1) to apply an electrical potential to a seed-layer on the workpiece. The electroplating machine 100 can also include a transfer mechanism 120 having a rail or track 122 and a plurality of robots 124 that move along the track 122. The robots 124 include arms 126 that can carry a microelectronic workpiece 130 between the chambers 110. In operation, the load/unload mechanism 104 positions a cassette holding a plurality of workpieces in the cabinet 102, and the transfer mechanism 120 handles the individual workpieces 130 inside the cabinet 102. The transfer mechanism 120, for example, can initially place the workpiece 130 in an electroless plating chamber 114 to repair or enhance the seed-layer on the workpiece. The transfer mechanism 120 can then remove the workpiece 130 from the electroless plating chamber 114 and place it in the electroplating chamber 112 for forming a blanket layer or a patterned layer on the front face of the workpiece 130. In an alternative embodiment, the transfer mechanism can be a radial system such as in the EQUINOX® machines manufactured by Semitool, Inc. of Kalispell, Mont. After the electroplating cycle, the transfer mechanism 120 can remove the workpiece 130 from the electroplating chamber 112 and transfer it to another processing station in the machine 100 (e.g., a standard rinser-dryer, a rinse/etch capsule, an annealing chamber, etc.) or place it in the cassette.

Figure 2:
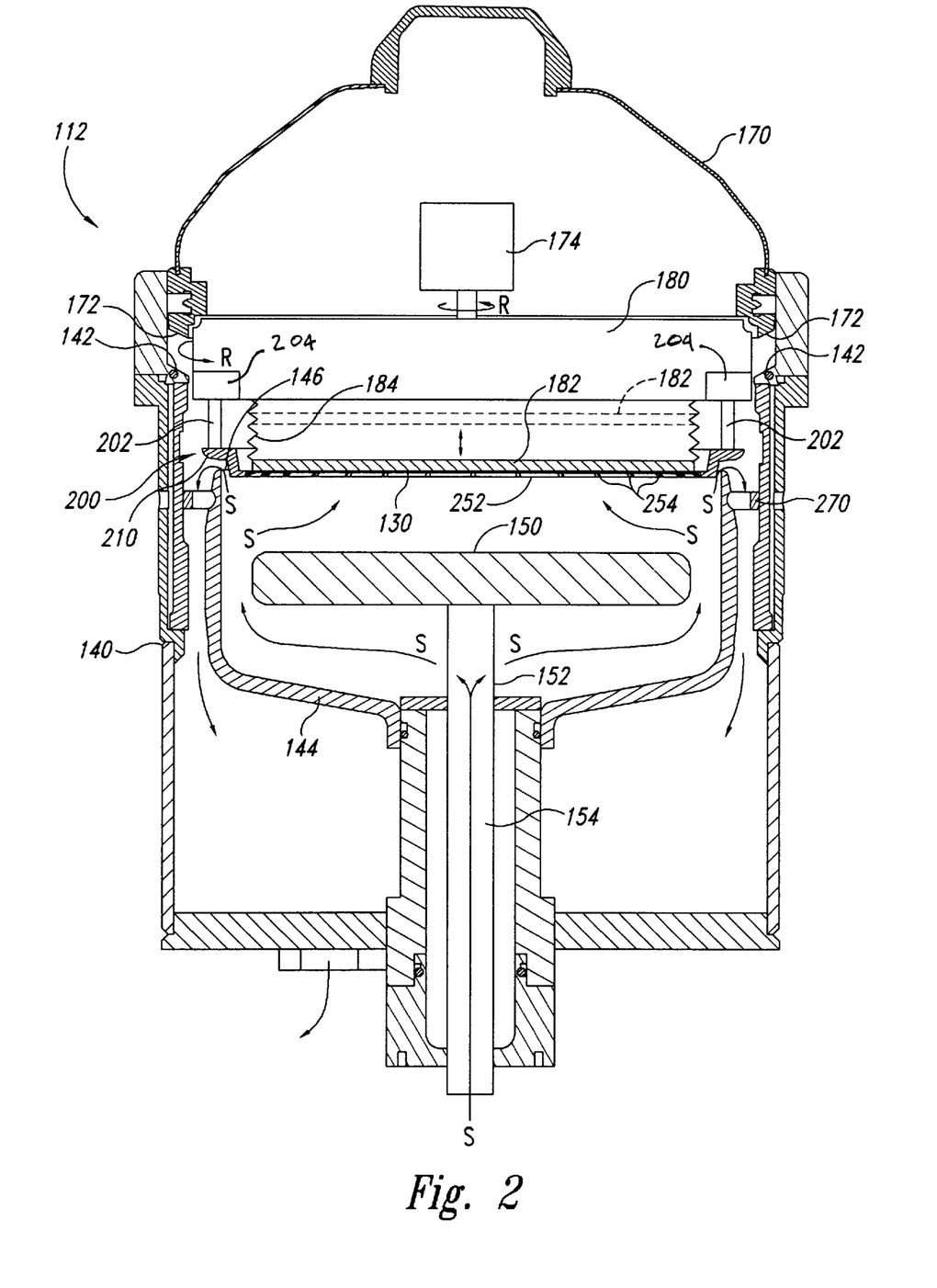
FIG. 2 is a cross-sectional view of an electroplating chamber having a contact assembly for use in an electroplating machine in accordance with an embodiment of the invention.

FIG. 2 is a partial cross-sectional view of an electroplating chamber 112 having a contact assembly 200 in accordance with one embodiment of the invention for supporting and providing an electrical connection to a front face of the workpiece 130. For the purposes of brevity, several components of the electroplating chamber 112 are shown schematically or by line drawings. Many of the particular features of the components shown schematically are described more detail in the patent applications incorporated by reference. The electroplating chamber 112 can include a bowl 140 configured to contain an electroplating solution, an anode 150 in the bowl 140, and a head assembly 170 that carries the contact assembly 200. The head assembly 170 is movable with respect to the bowl 140 to position the workpiece 130 in the plating solution (not shown). In the embodiment shown in FIG. 2, the head assembly 170 is shown in a partially inserted position in which the contact assembly 200 and the workpiece 130 are at a slight angle. When the head assembly 170 is fully inserted into the bowl 140, a beveled surface 172 of the head assembly 170 is superimposed over a corresponding beveled surface 142 of the bowl 140, and the contact assembly 200 holds the workpiece 130 in a desired position relative to the plating solution.

The bowl 140 can include a cup 144 having an overflow wier 146. The anode 150 is positioned in the cup 144, and the anode 150 can be attached to an anode support assembly 152. In one embodiment, the anode support assembly 152 has a channel 154 through which the electroplating solution flows and is discharged into the cup 144. The anode support assembly 152 can be electrically conductive, or it can include a conductor to electrically couple the anode 150 to a power supply. In operation, a flow of plating solution (identified schematically by arrows "S") passes through the anode support assembly 152 and is discharged into the cup 144 underneath the anode 150. The plating solution flow S continues around the anode 150, over the wier 146, and into a lower portion of the bowl 140. As the plating solution flow S passes over the wier 146, it forms a meniscus at the top of the cup 144. The plating solution flow S can then pass out of the bowl 140 where it is filtered and reconditioned so that the plating solution can be re-circulated through the cup 144. Suitable embodiments of bowls 140, cups 144, anodes 150 and anode support assemblies 152 are described in PCT Application Nos. PCT/US99/15430 and PCT/US00/10210, which are herein incorporated by reference.

The head assembly 170 can further include a motor 174 and a rotor 180 that carries the contact assembly 200. The motor 174 is coupled to the rotor 180 to rotate the contact assembly 200 and the workpiece 130 during a plating cycle (Arrow R). The rotor 180 can include a movable backing plate 182 and a seal 184. The backing plate 182 can move transverse to the workpiece 130 (Arrow T) between a first position in which the backing plate 182 engages the back side of the workpiece 130 (shown in solid lines in FIG. 2) and a second position in which it is spaced apart from the back side of the workpiece 130 (shown in broken lines in FIG. 2). In this embodiment, the contact assembly 200 is coupled to the rotor 180 by a plurality of shafts 202 that are received in quick-release mechanisms 204. The shafts 202 can be rigid, conductive members that electrically couple the contact assembly 200 to an electrical potential so that the seed-layer on the workpiece 130 is a cathode.

In operation, the head assembly 170 can be initially raised above the bowl 140 and rotated about a relatively horizontal axis to position the contact assembly 200 to face upward away from the bowl 140. The backing plate 182 is moved to the second position in which it is spaced apart from the contact assembly 200 to load the workpiece 130 into the head assembly 170. The robot 124 (FIG. 1) inserts the workpiece 130 face-up into the contact assembly 200, and then the backing plate 182 moves to the first position in which it presses the workpiece 130 against the contact assembly 200. The head assembly 170 then rotates about the horizontal axis to position the contact assembly 200 face downward and lowers the loaded workpiece 130 and a portion of the contact assembly 200 into the plating solution proximate to the overflow wier 146. The motor 174 rotates the rotor 180 about a relatively vertical axis to move the workpiece 130 in the plating solution during the plating cycle. After the plating cycle is complete, the head assembly 170 removes the workpiece 130 from the plating solution so that it can be rinsed and/or transferred to another processing chamber or machine. In an alternative embodiment, the head assembly does not rotate about the horizontal axis to position the contact assembly 200 face-up during a load/unload sequence such that the workpiece is loaded into the contact assembly face-down toward the bowl 140.

The foregoing description of the electroplating machine 100 and the electroplating chamber 112 provides examples of the types of devices in which contact assemblies in accordance with embodiments of the invention can be used to plate metal layers onto microelectronic workpieces. It will be appreciated that the contact assembly 200, and other embodiments of contact assemblies described in more detail below, can be used with other electroplating machines and reaction chambers.

B. Selected Embodiments of Contact Assemblies for Electroplating Microelectronic Workpieces FIGS. 3–11 illustrate several embodiment contact assemblies that can be used in the electroplating chamber 112 of the electroplating machine 100. The structures and operation of the contact assemblies shown in FIGS. 3–11 are generally described with reference to wet-contact assemblies. It will be appreciated, however, that they can also be configured to be dry-contact assemblies. Therefore, the basic structure is applicable to both wet-contact and dry-contact electroplating applications.

Figure 3:
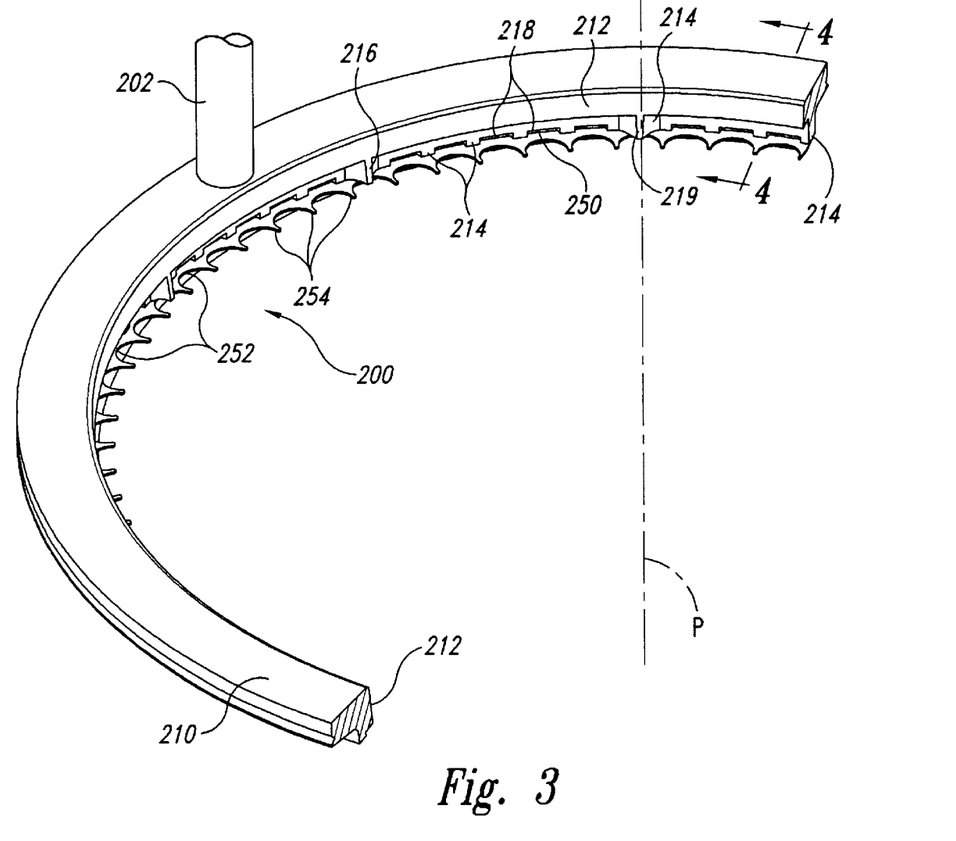
FIG. 3 is an isometric view illustrating a portion of a contact assembly for use in an electroplating machine in accordance with an embodiment of the invention.

FIG. 3 is an isometric view showing the features of an embodiment of the contact assembly 200 in greater detail. In this embodiment, the contact assembly 200 has a support member 210 and a contact system 250 attached to the support member 210. The shafts 202 can be connected to the support member 210 to attach the contact assembly 200 to the head assembly 170 (FIG. 2). The support member 210 can have a circular shape, a shape with one or more straight-edge sections, or any other suitable shape corresponding to the shape of the workpiece. The embodiment of the support member 210 shown in FIG. 2 is a ring having an inner wall 212 defining an opening that is configured to allow the workpiece 130 (FIG. 2) to move through the support member 210 along an access path "P." The support member 210 can be formed from a conductive material, such as titanium, stainless-steel, or another suitable metal. In an alternative embodiment, the support member 210 can be formed from a dielectric material and further include conductive lines extending through the dielectric material. In this embodiment, the support member 210 includes a plurality of posts 214 and workpiece guides 216. The posts 214 project downwardly from the main portion of the conductive ring, and the posts 214 can have squared corners or rounded corners. The posts 214 can also have rectilinear or circular cross-sections, and in one embodiment the posts are approximately 0.10–0.40 inch wide. The posts 214 are spaced apart from one another by gaps 218 that provide passageways for gas bubbles and electroplating solution to pass through the support member 210 during a plating cycle. In one particular embodiment, the gaps are approximately 0.10–0.30 inch high and 0.10–0.25 inch wide. The workpiece guides 216 can be positioned around the interior of the support member 210 at selected radial increments, such as 15°, 30°, 60°, etc. The workpiece guides 216 can have a tapered surface 219 that slopes into the opening for guiding the workpiece 130 onto the contact system 250. The workpiece guides 216 can include other embodiments or be arranged around the interior of the support member 210 in different patterns, and the posts 214 and the gaps 218 can have different sizes and shapes than those set forth above.

The contact system 250 can comprise a conductive mounting section 252 and a plurality of contact members 254 projecting from the mounting section 252 into the opening defined by the support member 210. The mounting section 252, for example, can be a ring that is connected to the posts 214 of the support member 210 by spot welds, screws, or other suitable techniques. The mounting section 252 can alternatively be a segment, such as an arcuate segment of a ring, and a plurality of separate segments can be attached to the posts 214 of the support member 210. The mounting section 252 and the contact members 254 can be formed from an electrically conductive material and/or have a suitable electrically conductive coating. In one embodiment, the mounting section 252 and a contact members 254 are made from a sheet of metal, such as titanium, stainless-steel, or another suitably conductive material that can flex under the loads generated by the backing plate 182 as it presses the workpiece 130 against the contact members 254.

The contact members 254 can be conductive biasing elements that project inwardly into the opening defined by the inner wall 212 of the support member 210 and transversely with respect to the access path P. In one embodiment, the contact members 254 are cantilevered spring elements. The contact members 254 can be integral with the mounting section 252, or they can be individual fingers that are attached to the mounting section 252 by spot welds or other suitable fasteners. In this embodiment, the contact members 254 are cantilevered spring elements or fingers that project inwardly along a radius of the support member 210.

Figure 4:
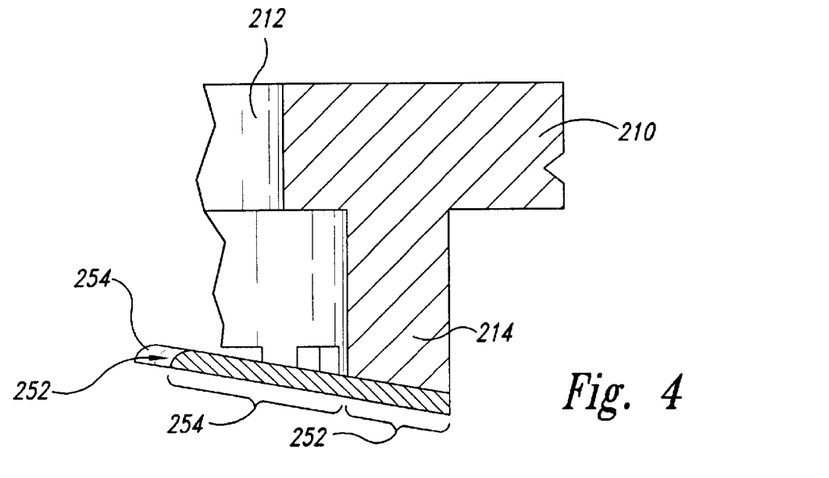
FIG. 4 is an isometric view illustrating a cross-section of a contact assembly for use in an electroplating machine in accordance with an embodiment of the invention.

FIG. 4 is a partial isometric view that illustrates an embodiment of the support member 210, the mounting section 252, and the contact members 254 in greater detail. The posts 214 of the support member 210 can have an angled lower surface that projects upwardly with respect to the access path P. Additionally, the mounting section 252 and the contact members 254 can be formed to have a conical shape that angles upwardly such that the contact members 254 also project upwardly with respect to the access path P. The upward angle is approximately 5°–15°, and more specifically can be approximately 8°. In an alternative embodiment, the support members 254 can extend approximately normal to the access path P. In operation, the backing member 182 (FIG. 2) drives the workpiece 130 downward along the access path P causing the contact members 254 to flex downwardly and slide transversely across the surface of the workpiece 130. The downward flexing of the contact members 254 allows the contact members 254 to conform to a topographical surface of the workpiece 130, and the sliding of the contact members 254 removes oxides that may have grown on the seed-layer.

Figures 5, 6, 7:
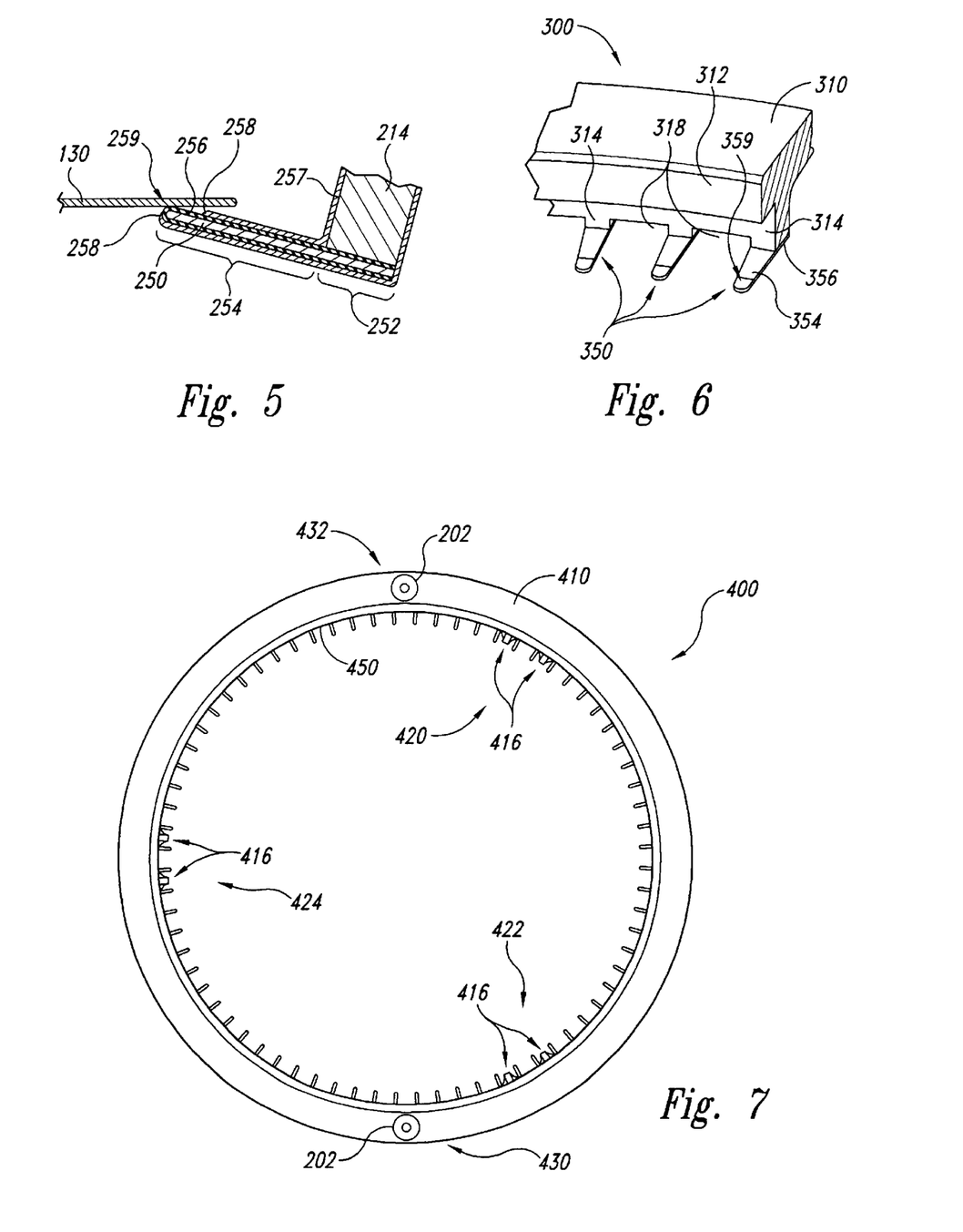
FIG. 5 is a cross-sectional view of a portion of the contact assembly of FIG. 4 illustrating a contact member in accordance with an embodiment of the invention in greater detail.
FIG. 6 is an isometric view illustrating a portion of a contact assembly for use in an electroplating machine in accordance with another embodiment of the invention.
FIG. 7 is top plan view of a contact assembly for use in an electroplating machine in accordance with another embodiment of the invention.

FIG. 5 is a cross-sectional view illustrating a portion of an embodiment of the contact assembly 200 that is particularly well-suited for use as a wet-contact assembly in which the contact system 250 and a portion of the support member 210 are submerged in a plating solution. In this embodiment, the mounting section 252 and the contact members 254 are stamped or otherwise formed from a sheet of titanium or another suitable conductive material so that the mounting section 252 and the contact members 254 are integral with one another. The mounting section 252 and the contact members 252 an be coated with a layer of a conductive contact material 256. One suitable metal for the contact layer 256 is platinum, but other metals that interact with the plating solution and the seed-layer in a desired manner can be used. The support member 210 and the contact system 250 can then be coated with a dielectric coating 257. The dielectric coating 257 is generally selected according to (a) the compatibility with the plating solution, (b) adhesion to the metal of the contact system 250, and (c) ability to effectively coat the contact system 250. Suitable materials that can be used for the dielectric coating 257 include (a) an 8840 primer and a Teflon dielectric exterior coating manufactured by DuPont® ("DuPont"); (b) an 8840 green coating manufactured by DuPont; (c) a 954-100 epoxy based coating manufactured by DuPont; (d) a 954-101 epoxy based coating manufactured by DuPont; (e) HALAR® coatings under the name Dycore® 404; (f) KYNAR® coatings under the identification Dycore® 202 either with or without a primer of Dycore 204; (g) HALAR® heavy coatings; (h) FLUO-ROLON® 109 distributed by Southwest Impreglon® Sales, Inc. of Texas; (i) Impreglon 216® or Impreglon 872® distributed by Southwest Impreglon® Sales, Inc.; and (j) other epoxy based coatings, thermoplastic copolymers, or fluorocarbon resins. It will be appreciated that other materials can be used for the dielectric coating 257, and thus the foregoing materials provide examples that are not intended to limit the claims.

The contact members 254 can also have an aperture 258 formed in the dielectric coating 257 at a contact site 259 to expose a portion of the contact layer 256. The aperture 258 can be formed by laser ablating techniques that consume the dielectric coating 257 to form stepped edges at the aperture 258. Laser ablating techniques can be closely controlled so that the dielectric coating 257 can be removed from the contact layer 256 without damaging or impairing the performance of the contact layer 256. For example, the energy and/or wavelength of the laser can be selected so that it consumes the dielectric coating 257 without affecting the contact layer 256. Additionally, the residence time that the laser impinges the dielectric coating 257 can be controlled so that the laser is moved before it consumes the contact layer 256. The aperture 258 can alternatively be formed using machining techniques. In either case, the dielectric coating 257 does not cover the contact site 259 so that the contact member 254 can provide an electrical potential to the seed-layer on the workpiece 130.

FIGS. 2 and 3 illustrate the operation and advantages of several embodiments of the contact assembly 200. Referring to FIG. 2, when the head assembly 170 rotates the workpiece 130, the plating solution at the front face of the workpiece 130 is driven radially outwardly toward the support member 210. Referring to FIG. 3, the plating solution and any gas bubbles at the surface of the workpiece 130 pass through the gaps 218 of the support member 210. An electrical potential is also applied to seed-layer on the workpiece via the contact system 250 to establish a current field between the anode 150 and the seed-layer. The current between the anode 150 and the seed-layer causes the metal in the plating solution to plate onto the seed-layer and portions of the contact members 254 because the contact members 254 are also exposed to the plating solution. After an adequate layer of metal has been plated onto the workpiece 130, the head assembly 170 raises the contact assembly 200 to an intermediate elevation at which a rinsing solution is applied to the workpiece 130 as it continues to rotate. The head assembly 170 is then raised to clear the upper lip of the bowl 140, and the workpiece 130 is removed from the contact assembly 200. The head assembly 170 can then be re-lowered to submerge the contact assembly 200 in the plating solution for de-plating the contact members 254 by switching the potential applied to the contact members 254 so that the contact members 254 are the anode and applying an opposite potential to a ring cathode 270 in the bowl 140.

When the contact assembly 200 is used in a wet-contact environment, several embodiments of the contact assembly 200 reduce galvanic etching of the seed-layer at the interface between the contact members and the seed-layer compared to dry-contact assemblies. Because the contact assembly 200 has contact members 254 coated with a dielectric material, it can be a "wet-contact" assembly in which the contact members 254 are exposed to the plating solution. The etching caused by the galvanic effect between the seed-layer and the contact members 254 before being immersed in the plating solution does not occur after the contact assembly 200 is placed in the plating solution. Therefore, several embodiments of the contact assembly 200 are expected to provide a uniform current distribution around the perimeter of the workpiece throughout a plating cycle to enhance the uniformity of the plated layer.

Several embodiments of the contact assembly 200 also provide a large number of contacts that uniformly engage the perimeter of the workpiece. Because the contact members 254 flex downwardly as the workpiece is loaded into the contact assembly 200, the contact members 254 can compensate for topographical variances across the surface of the workpiece to provide a uniform pressure against the various contact points on seed-layer. Additionally, the large number of individual contact members 254 enhance the uniformity of the electrical potential around the perimeter of the workpiece. Therefore, several embodiments of the contact assembly 200 are expected to further enhance the uniformity of the plated layer by providing a large number of contact members 254 that can adapt to different topographical features on the workpiece.

Several embodiments of the contact assembly 200 used for wet-contact applications reduce non-uniformities caused by bubbles in the plating solution. One problem of electroplating is that bubbles can form on the anode 150 (FIG. 2) and rise through the plating solution to the face of the workpiece 130. Air can also be trapped on the face of the workpiece 130 as it is lowered into the plating solution. As the workpiece 130 rotates through the plating solution, the bubbles are driven radially outward toward the perimeter of the workpiece. If the bubbles are trapped at the perimeter of the workpiece, they can prevent the plating solution from contacting the workpiece in a manner that causes non-uniform plating. The contact assembly 200 mitigates this problem because any such bubbles can flow through the gaps 218 between the posts 214 of the support member 210. Therefore, several embodiments of the contact assembly 200 are expected to reduce non-uniformities caused by bubbles in the plating solution.

Selected embodiments of the contact assembly 200 also enhance the uniformity of the electrical interface between the contact members 254 and the seed-layer by mechanically impairing the metal from plating over the dielectric coating 257 adjacent to the contact sites 259. Another problem of using a conventional wet-contact assembly is that the metal can plate over the dielectric coating during the plating cycle. The metal that plates over the dielectric coating may not be completely removed during a de-plating cycle, or it can increase the duration of the de-plating cycle causing a reduction in throughput of the electroplating machine. In embodiments of the contact assembly 200 in which the dielectric coating 257 is removed from the contact sites 259 using laser ablating techniques, the stepped edge of the aperture 258 creates a step-height that inhibits the metal from plating onto the dielectric coating 257 adjacent to the aperture 258. Laser ablated apertures 258 accordingly eliminate or at least reduce the amount of metal that must be removed by the de-plating process. Therefore, certain embodiments of the contact assembly 200 are expected to enhance the efficacy of de-plating processes to provide a more consistent electrical interface between the contact members 254 and the seed-layer.

FIG. 6 is a partial isometric view of a contact assembly 300 in accordance with another embodiment of the invention. The contact assembly 300 can include a support member 310 and a contact system 350 comprising a plurality of individual, separate contact members 354. The support member 310 can be substantially similar to the support member 210 described above. The support member 310 can accordingly have an inner wall 312 defining an opening configured to receive the workpiece 130 and a plurality of posts 314 that are spaced apart from one another by gaps 318. The individual contact members 354 can be similar to the contact members 254 described above with reference to FIGS. 4 and 5, except that the individual contact members 354 have individual mounting sections 356 attached to the posts 314 by spot welds or other suitable fasteners. The contact system 350 accordingly does not include a mounting section spanning between the posts 314. The support member 310 and the contact members 354 can be coated with the same coatings described above with reference to FIGS. 4 and 5. The contact assembly 300 operates in a manner that is similar to the contact assembly 200 described above, and several embodiments of the contact assembly 300 may also provide similar advantages as the contact assembly 200.

FIG. 7 is a top plan view of a contact assembly 400 in accordance with another embodiment of the invention. The contact assembly 400 can include a support member 410 and a contact system 450 attached to the support member 410. The support member 410 can be a conductive ring having a plurality of downwardly depending posts (not shown in FIG. 7) that are separated from one another by gaps similar to the posts 214 shown in FIG. 3.

The support member 410 also has a plurality of guides 416 that are arranged in a first guide pair 420, a second guide pair 422, and a third guide pair 424. In this embodiment, the guide pairs 420, 422, and 424 are spaced apart from one another by approximately 120° around the interior of the support member 410. The first guide pair 420 can be spaced 60° apart from one of the contact shafts 202, and the second guide pair 422 can be spaced 60° apart from the other contact shaft 202 on the same side of the support member 410. The third guide pair 424 can be spaced equally between the contact shafts 202 on the other side of the support member 410. This spacing of the guide pairs inhibits the plating solution from wicking up the guides 416 and onto the back side of the workpiece as the head assembly 170 (FIG. 2) lowers one side of the contact assembly 400 into the plating solution at an angle relative to the overflow wier 146 (see the contact assembly 200 shown in FIG. 2). For example, if the contact assembly 400 shown in FIG. 7 is attached to the head assembly 170 shown in FIG. 2 so that a first region 430 of the contact assembly 400 is lowered into the plating solution and then a second region 432 is the final portion of the contact assembly 400 lowered into the solution, then the guides 416 are spaced apart from the first region 430 so that the plating solution does not wick up between the guides 416 and the workpiece. If the guides 416 were located at the first region 430, then the plating solution may wick up the guides and onto the backside of the workpiece.

The guides 416 are not limited to the arrangement shown in FIG. 7. The guides 416, for example, can be arranged individually or in pairs so that the guides 416 are generally spaced apart from the portion of the contact assembly that is (a) initially submerged in the plating solution and/or (b) submerged to the greatest depth in the plating solution. Therefore, the contact assembly 400 may have additional embodiments that inhibit contamination of the backside of the workpiece caused by wicking of the plating solution.

Figure 8:
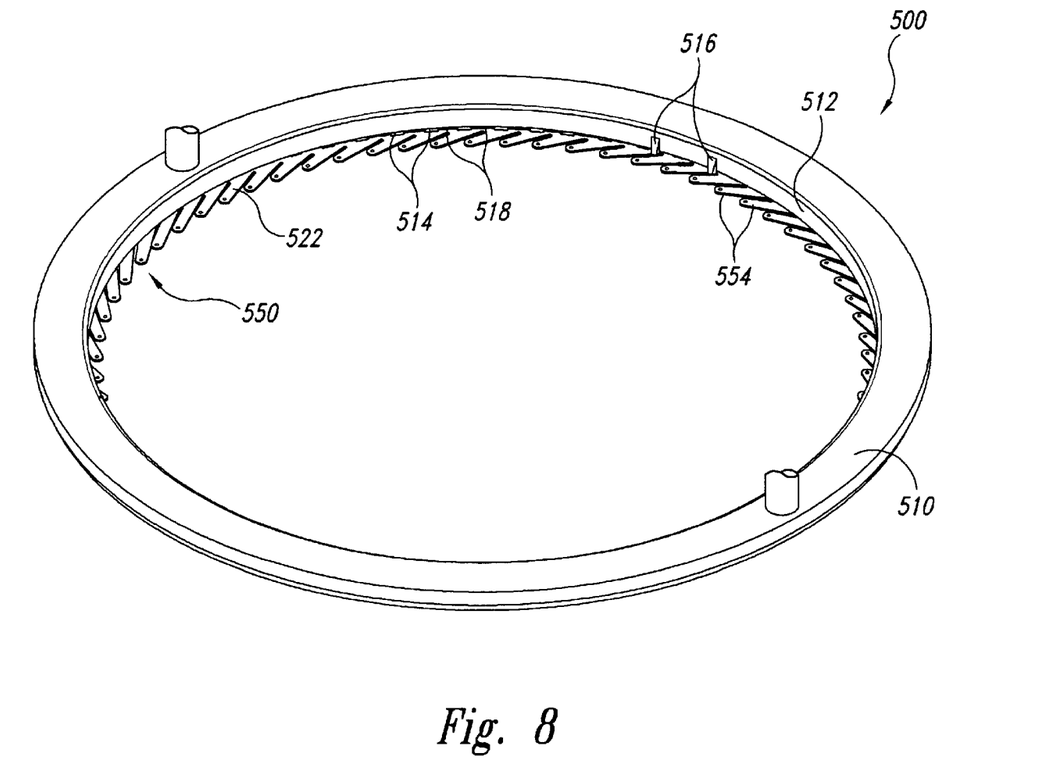
FIG. 8 is an isometric view of a contact assembly for use in an electroplating machine in accordance with another embodiment of the invention.

FIG. 8 is an isometric view of a contact assembly 500 in accordance with another embodiment of the invention for use in a reactor chamber of a plating machine. The contact assembly 500 can have a support member 510 and a contact system 550 comprising a plurality of swept or angled contact members 554. The support member 510 can have an inner wall 512 defining an opening for receiving the workpiece, a plurality of posts 514 spaced apart from one another by gaps 518, and a plurality of guides 516 arranged around the inner wall 512. The posts 514 can be substantially the same as the posts 214, and the guides 516 can be arranged as set forth above in FIG. 3 or 7. In FIG. 8, more specifically, the guides 516 are arranged in guide pairs to inhibit wicking of the plating solution. The contact system 550 is attached to the posts 514 of the support member 510 so that bubbles can flow through the gaps 518 in the support member 510.

Figure 9:
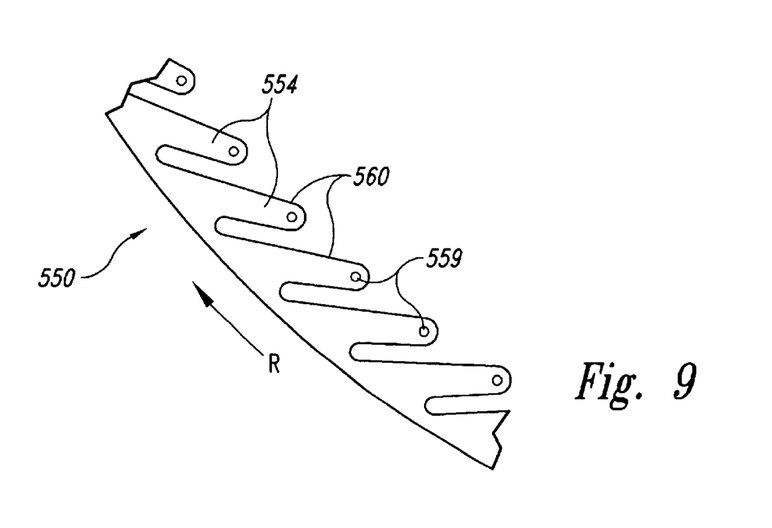
FIG. 9 is a top plan view of a contact system for use in a contact assembly in accordance with an embodiment of the invention.

FIG. 9 is a top plan view illustrating a portion of an embodiment of the contact system 550 in greater detail. Referring to FIGS. 8 and 9 together, the contact system 550 can further comprise a mounting section 552, such as an arcuate ring, a segment of an arcuate ring, or another structure for mounting the contact members 554 to the support structure 510. The contact members 554 can project from the mounting section 552 inwardly into the opening of the support member 510 at an angle relative to a radius of the support member 510. Additionally, the contact members 554 can project upwardly in a manner similar to the contact member 254 shown in FIG. 4. The support member 510 and the contact system 550 can be made from and coated with the materials set forth above with respect to the contact assembly 200. As such, the contact members 554 can have a contact site 559 for contacting the seed-layer on the workpiece.

The contact assembly 500 is expected to provide a good electrical connection between the contact members 554 and the seed-layer on the workpiece. One aspect of plating microelectronic workpieces is that the real estate on the front face of the workpiece should be used to form features, and thus the contact members 554 should not extend too far inward from the perimeter of the workpiece. It is also generally desirable that the contact members have a relatively long lever arm so that they flex easily as the workpiece presses against them. The contact system 550 provides a solution to increase the length of the lever arm of the contact member 554 without extending further inwardly beyond the perimeter of the workpiece by angling the contact member 554 relative to diametric lines of the support member 510. Therefore, the contact members 554 have desirable flexural qualities without affecting the available real estate on the workpiece for fabricating devices.

The contact assembly 500 is also expected to provide a desirable flow of the plating solution at the perimeter of the workpiece. In operation, the workpiece is rotated in a direction R so that the inward edges 560 of the contact members 554 drive the plating solution toward the interior of the workpiece. The swept contact members 554 accordingly drive the plating solution away from the perimeter, and the swept contact members 554 are expected to produce less turbulence at the perimeter than radially projecting contact members. As a result, the swept contact members 554 are expected to provide a desirable flow of the plating solution at the perimeter of the workpiece.

Figure 10:
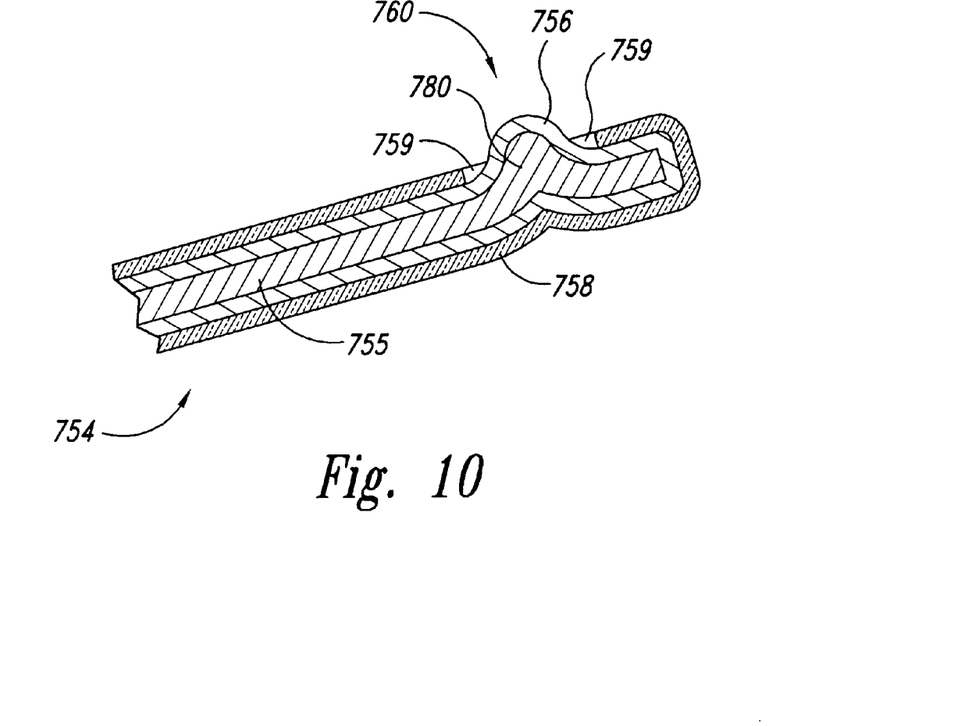
FIGS. 10 and 11 are cross-sectional views of contact members for contact assemblies in accordance with additional embodiments of the invention.

FIG. 10 is a cross-sectional view of a contact member 754 comprising a biasing element 755 having a raised feature 780 at a contact site 760 for contacting the seed-layer of the workpiece. The biasing element 755 can be a finger made from titanium or another suitable conductive material with desirable structural qualities. A conductive contact layer 756 can coat the biasing element 755, and a dielectric coating 758 can cover the contact layer 756. The contact layer 756 can be platinum or another suitable metal, and the dielectric coating 758 can be one of the coatings described above. The dielectric coating 758 can be removed from the contact site 760 to expose the contact layer 756 on the raised feature 780 using a laser ablation technique. As a result, the dielectric coating 758 can have an aperture 759 with a stepped edge to inhibit the metal in the plating solution from plating over the dielectric coating 758 adjacent to the aperture 759. In this embodiment, the raised feature 780 is a deformed portion of the biasing element 755, and the contact layer is a conformal layer that is plated onto the biasing element 755.

Figure 11:
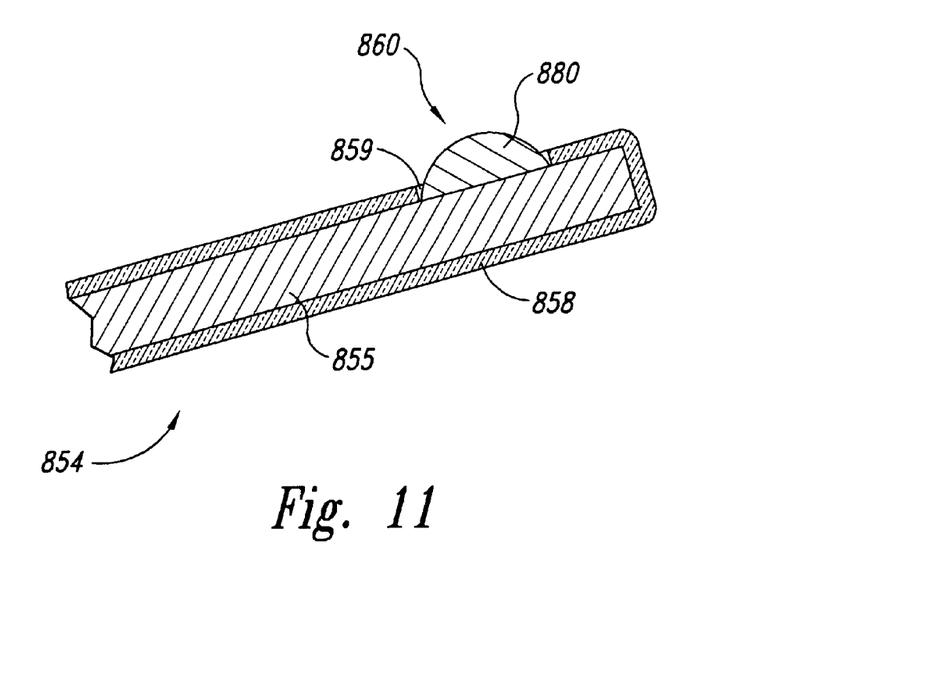

FIG. 11 is a cross-sectional view of a contact member 854 having a biasing element 855 with a raised feature 880 at a contact site 860. The biasing element 855 can be a finger that is coated with a dielectric layer 858. In this embodiment, the dielectric layer 858 has an aperture 859 at the contact site 860, and the raised feature 880 is a bump of contact material deposited at the contact site 860. The raised feature 880, for example, can be a platinum bump. The contact members 254, 354 and 554 described above can have the structure of the contact members 754 or 854 shown in FIGS. 10 and 11.

Several embodiments of the contact member 754 an 854 are expected to provide a more consistent, uniform electrical connection between the contact assembly and the seed-layer in wet-contact plating processes. The raised features on the contact members space the workpiece apart from the contact members so that the plating solution can flow more easily adjacent to the contact points. The increased flow of the plating solution reduces the size of the diffusion layer at the contact points in a manner that reduces plating onto the contact sites and over the dielectric coating adjacent to the contact sites. Such a reduction in plating at the contact sites should provide a consistent electrical connection throughout a plating cycle to provide a more uniform current distribution around the perimeter of the workpiece. Also, a reduction in plating on the contact members is expected to reduce the time expended for de-plating the contact assembly. Thus, contact members with raised features should increase both the uniformity of the current distribution and the throughput of electroplating processes.

From the foregoing it will be appreciated that specific embodiments of the invention have been described herein for purposes of illustration, but that various modifications may be made without deviating from the spirit and scope of the invention. Accordingly, the invention is not limited except by the appended claims.

The claimed subject matter is:

1. A reactor for electrochemical deposition processing of microelectronic workpieces, comprising:
    a bowl configured to hold a plating solution;
    an anode in the bowl at a location to contact the plating solution;
    a head assembly moveable relative to the bowl between a first position to load/unload a workpiece and a second position to place at least a portion of the workpiece in the plating solution; and
    a contact assembly comprising a support member and a contact system, wherein
        the support member has an inner wall defining an opening configured to allow the workpiece to move through the support member along an access path, and
        the contact system is coupled to the support member, wherein the contact system has a plurality of contact members projecting inwardly into the opening relative to the support member and transversely with respect to the access path, and wherein each contact member has a contact site configured to electrically contact the workpiece and a dielectric coating around the contact site.

2. The reactor of claim 1 wherein the contact members comprise cantilevered spring elements projecting upwardly into the opening.

3. The reactor of claim 1 wherein the contact members comprise cantilevered spring elements projecting upwardly into the opening, and the cantilevered spring elements have a raised feature.

4. The reactor of claim 1 wherein the contact members comprise cantilevered spring elements projecting upwardly into the opening, and the cantilevered spring elements have a raised feature comprising a deformed section of the spring elements.

5. The reactor of claim 1 wherein the contact members comprise cantilevered spring elements projecting upwardly into the opening, and the cantilevered spring elements have a raised feature comprising a bump of a separate material on the spring elements.

6. The reactor of claim 1 wherein:
    the support member comprises a ring and a plurality of posts depending from the ring that are separated from one another by gaps; and
    the contact assembly further comprises a conductive arcuate element attached directly to the posts to define flow paths through the gaps and the contact members comprise fingers integral with the arcuate element that project inwardly into the opening along a radius of the ring.

7. The reactor of claim 1 wherein:
    the support member comprises a ring and a plurality of posts depending from the ring that are separated from one another by gaps; and
    the contact assembly further comprises a conductive arcuate element attached directly to the posts to define flow paths through the gaps and the contact members comprise fingers integral with the arcuate element that project inwardly into the opening along a radius of the ring, and wherein the fingers have a raised contact feature.

8. The reactor of claim 1 wherein:
    the support member comprises a ring and a plurality of posts depending from the ring that are separated from one another by gaps; and
    the contact assembly further comprises a conductive arcuate element attached directly to the posts to define flow paths through the gaps and the contact members comprise fingers integral with the arcuate element that project inwardly into the opening at an angle relative to a radius of the ring.

9. The reactor of claim 1 wherein:
    the support member comprises a ring and a plurality of posts depending from the ring that are separated from one another by gaps; and
    the contact assembly further comprises a conductive arcuate element attached directly to the posts to define flow paths through the gaps and the contact members comprise fingers integral with the arcuate element that project inwardly into the opening at an angle relative to a radius of the ring, and wherein the fingers have a raised feature.

10. A reactor for electrochemical deposition processing of microelectronic workpieces, comprising:
    a bowl configured to hold a plating solution;
    an anode in the bowl at a location to contact the plating solution;
    a head assembly moveable relative to the bowl between a first position to load/unload a workpiece and a second position to place at least a portion of the workpiece in the plating solution; and
    a contact assembly comprising a support member and a contact system, wherein
        the support member has an inner wall defining an opening configured to allow the workpiece to move through the support member along an access path; and the contact system is coupled to the support member, wherein the contact system comprises a plurality of contact members positioned inwardly into the opening relative to the support member to contact a peripheral portion of the workpiece, and wherein the contact members are configured to be immersed in a plating solution during a plating cycle.

11. The reactor of claim 10 wherein the contact members comprise cantilevered spring elements projecting upwardly into the opening, a contact site on the spring elements, and a dielectric coating on the spring elements that is configured to expose that contact sites.

12. The reactor of claim 11 wherein the cantilevered spring elements have a raised feature.

13. The reactor of claim 11 wherein the cantilevered spring elements have a raised feature comprising a deformed section of the spring elements.

14. The reactor of claim 11 wherein the cantilevered spring elements have a raised feature comprising a bump of a separate material on the spring elements.

15. The reactor of claim 10 wherein:
the support member comprises a conductive support ring; and
the contact system further comprises a conductive mounting section attached directly to the support ring, the contact members are fingers integral with the mounting section, and each finger has a contact site configured to electrically contact the workpiece.

16. The reactor of claim 15 wherein the mounting section comprises an arcuate element and the fingers project inwardly from the arcuate element along a radius of the support ring, and the fingers have a raised contact feature at the contact sites.

17. The reactor of claim 15 wherein the mounting section comprises an arcuate element and the fingers project inwardly from the arcuate element at an angle relative to a radius of the support ring, and the fingers have a raised contact feature at the contact sites.

18. The reactor of claim 10 wherein:
the support member comprises a ring and a plurality of posts depending from the ring that are separated from one another by gaps;
the contact assembly further comprises a conductive arcuate element attached directly to the posts to define flow paths through the gaps and the contact members comprise fingers integral with the arcuate element that project inwardly into the opening; and
the support member and the contact assembly are coated with a dielectric coating that is configured to expose contact sites on the fingers.

19. The reactor of claim 18 wherein the fingers project inwardly into the opening along a radius of the ring and have a raised contact feature.

20. The reactor of claim 18 wherein the fingers project inwardly into the opening at an angle relative to a radius of the ring.

21. The reactor of claim 18 wherein the fingers project inwardly into the opening at an angle relative to a radius of the ring and have a raised feature.

22. A reactor for electrochemical deposition processing of microelectronic workpieces, comprising:
a bowl configured to hold a plating solution;
an anode in the bowl at a location to contact the plating solution;
a head assembly moveable relative to the bowl between a first position to load/unload a workpiece and a second position to place at least a portion of the workpiece in the plating solution; and
a contact assembly comprising a conductive support member and a contact system, wherein
the conductive support member has an inner wall defining an opening configured to allow the workpiece to move through the support member along an access path; and
the contact system comprising an arcuate mounting section coupled to the support member, a plurality of conductive cantilevered spring elements projecting from the arcuate mounting section inwardly into the opening relative to the support member and transversely with respect to the access path, a dielectric coating covering at least a portion of the spring elements, and an electrically conductive contact site on each spring element exposed through the dielectric coating.

23. A reactor for electrochemical deposition processing of microelectronic workpieces, comprising:
a bowl configured to hold a plating solution;
an anode in the bowl at a location to contact the plating solution;
a head assembly moveable relative to the bowl between a first position to load/unload a workpiece and a second position to place at least a portion of the workpiece in the plating solution; and
a contact assembly comprising a support member and a contact system, wherein
the support member has an inner wall defining an opening configured to allow the workpiece to move through the support member along an access path; and
the contact system is coupled to the support member, wherein the contact system comprises a plurality of contact members positioned inwardly into the opening relative to the support member to contact a peripheral portion of the workpiece, and wherein the contact members comprise electrically conductive fingers and raised contact sites projecting from the fingers.

24. The reactor of claim 23 wherein the raised contact sites comprise a deformed section of the fingers.

25. The reactor of claim 23 wherein the raised contact sites comprise a bump of a separate material on the fingers.

26. The reactor of claim 23 wherein:
the support member comprises a ring and a plurality of posts depending from the ring that are separated from one another by gaps; and
the contact assembly further comprises a conductive arcuate element attached directly to the posts to define flow paths through the gaps and the fingers are integral with the arcuate element, wherein the contact assembly is coated with a dielectric coating configured to expose contact sites on the fingers.

27. The reactor of claim 23 wherein the fingers project inwardly into the opening along a radius of the ring.

28. The reactor of claim 23 wherein the fingers project inwardly into the opening at an angle relative to a radius of the ring.

29. A reactor for electrochemical deposition processing of microelectronic workpieces, comprising:
a bowl configured to hold a plating solution;
an anode in the bowl at a location to contact the plating solution;
a head assembly moveable relative to the bowl between a first position to load/unload a workpiece and a second position to place at least a portion of the workpiece in the plating solution; and a contact assembly comprising a support member and a contact system, wherein the support member has a first section and a second section depending from the first section, the first section having an inner wall defining an opening configured to allow the workpiece to move through the support member along an access path, and the second section being defined by a plurality of posts depending from the first section, wherein the posts are separated from one another by gaps; and the contact system is coupled to the posts of support member, wherein the contact system comprises a plurality of contact members projecting inwardly into the opening relative to the support member to contact a peripheral portion of the workpiece.

30. An apparatus for electrochemical deposition, comprising:

a cabinet;

an electroplating chamber in the cabinet, the electroplating chamber comprising a bowl configured to hold a plating solution, an anode in the bowl at a location to contact the plating solution, a head assembly moveable relative to the bowl, and a contact assembly comprising a support member and a contact system, wherein the support member has an inner wall defining an opening configured to allow the workpiece to move through the support member along an access path, and the contact system is coupled to the support member, wherein the contact system has a plurality of contact members projecting inwardly into the opening relative to the support member and transversely with respect to the access path, and wherein the contact members have a contact site configured to electrically contact the workpiece and a dielectric coating around the contact site.

31. An apparatus for electrochemical deposition, comprising:

a cabinet;

an electroplating chamber in the cabinet, the electroplating chamber comprising a bowl configured to hold a plating solution, an anode in the bowl at a location to contact the plating solution, a head assembly moveable relative to the bowl, and a contact assembly comprising a support member and a contact system, wherein the support member has an inner wall defining an opening configured to allow the workpiece to move through the support member along an access path; and the contact system is coupled to the support member, wherein the contact system comprises a plurality of contact members positioned inwardly into the opening relative to the support member to contact a peripheral portion of the workpiece, and wherein each contact member has a raised feature at a contact site.

32. An apparatus for electrochemical deposition, comprising:

a cabinet;

an electroplating chamber in the cabinet, the electroplating chamber comprising a bowl configured to hold a plating solution, an anode in the bowl at a location to contact the plating solution, a head assembly moveable relative to the bowl, and a contact assembly comprising a support member and a contact system, wherein the support member has a first section and a second section depending from the first section, the first section having an inner wall defining an opening configured to allow the workpiece to move through the support member along an access path, and the second section being defined by a plurality of posts depending from the first section, wherein the posts are separated from one another by gaps; and the contact system is coupled to the posts of support member, wherein the contact system comprises a plurality of contact members projecting inwardly into the opening relative to the support member to contact a peripheral portion of the workpiece.

* * * * *

UNITED STATES PATENT AND TRADEMARK OFFICE
CERTIFICATE OF CORRECTION

PATENT NO. : 6,527,925 B1  
DATED : March 4, 2003  
INVENTOR(S) : Batz, Jr. et al.

It is certified that error appears in the above-identified patent and that said Letters Patent is hereby corrected as shown below:

Column 8,  
Line 41, "252 an" should be -- 254 can --;

Column 13,  
Line 46, insert hyphen after "wherein";

Column 16,  
Lines 4 and 28, insert hyphen after "wherein";  
Line 9, "comprising" should be -- comprises --;

Column 17,  
Lines 4 and 29, insert hyphen after "wherein";

Column 18,  
Lines 9 and 27, insert hyphen after "wherein";

Signed and Sealed this

First Day of July, 2003

JAMES E. ROGAN  
*Director of the United States Patent and Trademark Office*